(12) United States Patent
Wang

(10) Patent No.: US 7,227,019 B2
(45) Date of Patent: Jun. 5, 2007

(54) PROCESS FOR THE PREPARATION OF REBECCAMYCIN AND ANALOGS THEREOF

(75) Inventor: Jianji Wang, Dayton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 532 days.

(21) Appl. No.: 10/489,625

(22) PCT Filed: Sep. 13, 2002

(86) PCT No.: PCT/US02/29374

§ 371 (c)(1),
(2), (4) Date: Jul. 21, 2004

(87) PCT Pub. No.: WO03/022861

PCT Pub. Date: Mar. 20, 2003

(65) Prior Publication Data

US 2004/0248892 A1 Dec. 9, 2004

(51) Int. Cl.
*C07H 19/00* (2006.01)
*C07H 19/22* (2006.01)
*C07G 17/00* (2006.01)
*C07D 487/00* (2006.01)

(52) U.S. Cl. .................. 536/27.1; 536/18.7; 536/22.1; 536/124; 548/417

(58) Field of Classification Search .............. 536/18.7, 536/22.1, 27.1, 124; 548/417
See application file for complete search history.

(56) References Cited

U.S. PATENT DOCUMENTS 5,922,860 A * 7/1999 Kojiri et al. ............... 536/27.1

* cited by examiner

*Primary Examiner*—Shaojia Anna Jiang
*Assistant Examiner*—Traviss C. McIntosh, III
(74) *Attorney, Agent, or Firm*—Elliot Korsen

(57) ABSTRACT

The present invention relates to a method for making an indolopyrrolocarbazole of the general formula [I], where the method includes the step of reacting a bisindolylmaleimide compound with an oxidizing agent in the presence of an oxygen containing gas at a temperature and for a time sufficient to yield the indolopyrrolocarbazole compound of the general formula [I]. Methods of making rebeccamycin analogs using the indolopyrrolocarbazole compound are also provided

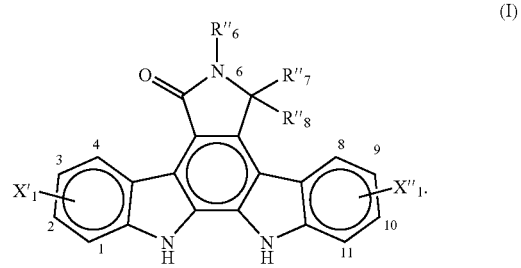

23 Claims, No Drawings

PROCESS FOR THE PREPARATION OF REBECCAMYCIN AND ANALOGS THEREOF

BACKGROUND OF THE INVENTION

1. Field of the Invention

The present invention relates generally to indolopyrrolocarbazoles and analogs thereof, more particularly to improved methods of making indolopyrrolocarbazoles and analogs thereof and their use as intermediates in the production of rebeccamycin and related analogs.

2. Description of the Background Art

Rebeccamycin and analogs thereof possess potent pharmaceuticaly activity especially the inhibition of tumor cell growth. For this reason, rebeccamycin and its analogs have been extensively studied for practical use as antitumor agents. The biologically active compounds are generally comprised of two components: an indolopyrrolocarbazole ring also referred to as rebeccamycin aglycone, and a sugar moiety which is covalently bonded to the ring. It is known that the biological activity of the compounds is closed associated with the rebeccamycin aglycone. Extensive research of the rebeccamycin aglycone has spurred a demand to find an efficient process of producing commercial quantities of the rebeccamycin aglycone and its analogs in a cost effective manner.

Several approaches to synthesizing rebeccamycin aglycone and its analogs have been reported in literature. See, for example, Gribble et al., *Tetrahedron*, 48, 8869 (1992), Moody et al., *J. Org. Chem.*, 57, 2105 (1992), and Joyce et al., *J. Org. Chem.*, 52 1177 (1987). It is known to react bisindolylmaleimides with oxidizing agents to synthesize the indolopyrrolocarbazole ring. Suitable oxidizing agents include dicyanodichloroquinone (DDQ), cupric chloride ($CuCl_2$), cupric acetate ($Cu(OAc)_2$), palladium chloride ($PdCl_2$), palladium diacetate ($Pd(OAc)_2$) and the like. The reaction rates and the availability of bisindolylmaleimides provide an efficient synthesis of the indolopyrrolocarbazole ring. However, these syntheses utilizing oxidizing agents have some limitations. For example, the use of DDQ as an oxidizing agent greatly complicates recovery of the desired product due to the products poor solubility. Iodine or cupric chloride used as oxidizing agents typically generate excessive by-products which significantly reduces overall yield and quality of the product.

It has been noted in the art that $Pd(O_2OCCF_3)$ and palladium diacetate $Pd(OAc)_2$ can suitably be used as oxidizing agents for synthesis of rebeccamycin aglycone. However, such oxidizing agents must often be used in excess to achieve acceptable oxidation levels. For example, palladium diacetate is capable of oxidizing bisindolylmaleimides to produce indolopyrrolocarbazole rings in acceptable yield levels, but at a level of 2.5 equivalents or 250 mol % of palladium diacetate. The need to use large amounts of the precious catalyst renders large-scale production of indolopyrrolocarbazole rings commercially impracticable.

Accordingly, there is a need for a method of making indolopyrrolocarbazoles rings such as indolo[2,3-a]pyrrolo[3,4-c]carbazoles in relatively high yields and with improved purity. It would be desirable to develop a process that is also low cost, and simple to perform. It would also be desirable to provide processes for making indolo[2,3-a]pyrrolo[3,4-c]carbazoles which may be used to provide a convenient source of intermediates for synthesizing biologically active compounds including rebeccamycin and analogs thereof.

SUMMARY OF THE INVENTION

The present invention is generally directed to a method of making rebeccamycin aglycone and related analogs also known as indolopyrrolocarbazole rings through oxidative cyclization of bisindolylmaleimide compounds. The present invention also encompasses processes of making rebeccamycin and related analogs employing the method of making rebeccamycin aglycone and related analogs.

In the application, unless otherwise specified explicitly or in context the following definitions apply. The numbers in the subscript after the symbol "C" define the number of carbon atoms a particular group can contain. For example, "$C_{1-6}$ alkyl" means a straight or branched saturated carbon chain having from one to six carbon atoms; examples include methyl, ethyl, n-propyl, isopropyl, n-buty, sec-butyl, isobutyl, t-butyl, n-pentyl, sec-pentyl, isopentyl, and n-hexytl. Depending on the context, "$C_{1-6}$ alkyl" can also refer to $C_{1-6}$ alkylene which bridges two groups; examples include propane-1,3-diyl, butane-1,4-diyl, 2-methyl-butane-1,4-diyl, etc. "$C_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_{2-6}$ alkenyl" can also refer to $C_{2-6}$ alkenediyl which bridges two groups; examples include ethylene-1,2-diyl (vinylene), 2-methyl-2-butene-1,4-diyl, 2-hexane-1,6-diyl, etc. "$C_{2-6}$-alkynyl" means a straight or branched carbon chain having at least one carbon-carbon triple bond, and from two to six carbon atoms; examples include ethynyl, propynyl, butynyl, and hexynyl.

"Aryl" means aromatic hydrocarbons having from six to ten carbon atoms; examles include phenyl and naphyl. "Substituted aryl" means aryl independently substituted with one to five (but preferably one to three) groups selected from $C_{1-6}$ alkanoyloxy, hydroxy, halogen, $C_{1-6}$alkyl, trifuloromethyl, $C_{1-6}$alkoxy, $C_{2-6}$ alkenyl, $C_{1-6}$alkanoyl, nitro, amino, cyano, azido, $C_{1-6}$alkylamino, di-$C_{1-6}$ alkylamino, and amido.

"Halogen" means flourine, chlorine, bromine, and iodine.

"Heteroaryl" means a five- or six-membered aromatic ring containing at least one and up to four non-carbon atoms selected from oxygen, sulfur, and nitrogen. Examples of heteroaryl include thienyl, furyl, pyrrolyl, imidazolyl, pyrazolyl, thiazolyl, thiadiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, and like rings.

The process of the present invention relates in part to the production of compounds of the general formula [I]:

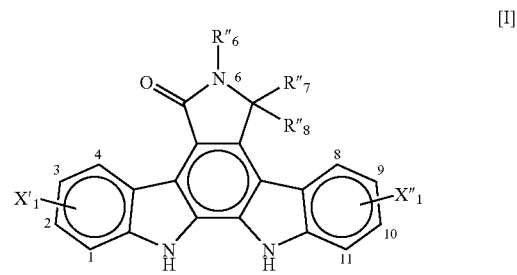

wherein:

independently selected $X'_1$ and $X''_1$ are at each of the 1-4 and 8-11 positions, respectively, and are selected from H, halogen, OH, —CN, CF$_3$, —COR"$_a$, NO$_2$, OR"$_{11}$, O(CH$_2$)$_n$ NR"$_9$R"$_{10}$, O(CH$_2$)$_n$OR"$_9$ and O(CH$_2$)$_n$COOR"$_9$;

n is an integer of from 0 to 4;

R"$_a$ is H, OH, C$_{1-7}$ alkoxy or NR"$_9$R"$_{10}$;

R"$_9$ and R"$_{10}$ are independently H, C$_{1-7}$alkyl, C$_{1-7}$ cycloalkyl, phenyl, benzyl, aryl, heteroaryl, any of which groups except hydrogen can be substituted with one to six of the same or different halogen, OH, NH$_2$, CN, NO$_2$, —C(=NH)NH$_2$, —CH(=NH), CH(R"$_b$) (CH$_2$)$_n$ COOH, CH(R"$_b$)(CH$_2$)$_n$ NH$_2$, COOR"$_{12}$, or R"$_9$ and R"$_{10}$ together with the nitrogen atom to which they are attached form a cyclic 5-8 membered non-aromatic ring containing either one or two heteroatoms selected from O, N, or S or R"$_9$ and R"$_{10}$ together form =CHR"$_{11}$R"$_{12}$;

R"$_b$ is H or COOH;

R"$_{11}$ and R"$_{12}$ are each independently hydrogen, C$_{1-7}$ alkyl, C$_{1-7}$ cycloalkyl, heteroaryl, non-aromatic cyclic 5-8 membered ring containing either one or two heteroatoms selected from O or N, (CH$_2$)$_n$ NR"$_9$R"$_{10}$, (CH$_2$)$_n$OR"$_9$ or (CH$_2$)$_n$COOR"$_9$, said C$_{1-7}$ alkyl being optionally substituted with one to six of the same or different halogen, OH, CN, NO$_2$, aryl or heteroaryl, said aryl or heteroaryl substitued with one or two groups independently selected from NR"$_9$R"$_{10}$, OH, COOR"$_9$, SO$_3$R"$_9$ or OCOR"$_9$;

n is 0 to 4;

R"$_6$ is H, C$_{1-7}$ alkyl, aryl, arylalkyl, OR"$_{10}$, NR"$_9$R"$_{10}$, or OCO(CH$_2$)$_n$NR"$_9$R"$_{10}$, said C$_{1-7}$ alkyl being optionally substituted with one to six of the same or different halogen, NR"$_9$R"$_{10}$, CN, NO$_2$, aryl, said aryl being substituted with one or two groups independetly selected from NR"$_9$R"$_{10}$, OH, COOR"$_9$, SO$_3$R"$_9$ or OCOR"$_9$; and R"$_7$ and R"$_8$ are each independently H, OH, or taken together is O.

In one aspect of the present invention, there is provided a method for making an indolopyrrolocarbazole compound of the general formula [I];

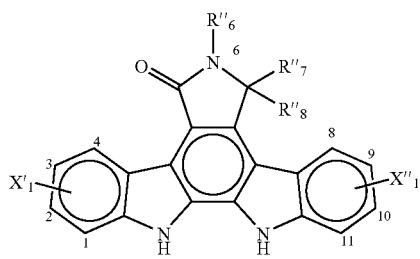

wherein:

independently selected $X''_1$ and $X''_1$ are at each of the 1-4 and 8-11 positions, respectively, and are selected from H, halogen OH, —CN, CF$_3$, —COR"$_a$, NO$_2$, OR", O(CH$_2$)$_n$ NR"$_9$R"$_{10}$, O(CH$_2$)$_n$OR"$_9$ and O(CH$_2$)$_n$COOR"$_9$;

n is an integer of from 0 to 4;

R"$_a$ is H, OH, C$_{1-7}$ alkoxy or NR"$_9$R"$_{10}$;

R"$_9$ and R"$_{10}$ are independently H, C$_{1-7}$ alkyl, C$_{1-7}$cycloalkyl, phenyl, benzyl, aryl, heteroaryl, any of which groups except hydrogen can be substituted with one to six of the same or different halogen, OH, NH$_2$, CN, NO$_2$, —C(=NH)NH$_2$, —CH(=NH), CH(R"$_b$) (CH$_2$)$_n$ COOH, CH(R"$_b$)(CH$_2$)$_n$ NH$_2$, COOR"$_{12}$, or R"$_9$ and R"$_{10}$ together with the nitrogen atom to which they are attached form a cyclic 5-8 membered non-aromatic ring containing either one or two heteroatoms selected from O, N, or S or R"$_9$ and R"$_{10}$ together form =CHR"$_{11}$R"$_{12}$;

R"$_b$ is H or COOH;

R"$_{11}$ and R"$_{12}$ are each independently hydrogen, C$_{1-7}$ alkyl, C$_{1-7}$ cycloalkyl, heteroaryl, non-aromatic cyclic 5-8 membered ring containing either one or two heteroatoms selected from O or N, (CH$_2$)$_n$ NR"$_9$R"$_{10}$, (CH$_2$)$_n$OR"$_9$ or (CH$_2$)$_n$ COOR"$_9$, said C$_{1-7}$ alkyl being optionally substituted with one to six of the same or different halogen, OH, CN, NO$_2$, aryl or heteroaryl, said aryl or heteroaryl substituted with one or tow groups independently selected from NR"$_9$R"$_{10}$, OH, COOR"$_9$, SO$_3$R"$_9$ or OCOR"$_9$;

R"$_6$ is H, C$_{1-7}$ alkyl, aryl, arylalkyl, OR"$_{10}$, NR"$_9$R"$_{10}$, or OCO(CH$_2$)$_n$NR"$_9$R"$_{10}$; said C$_{1-7}$ alkyl being optionally substituted with one to six of the same or different halogen, NR"$_9$R"$_{10}$, CN, NO$_2$, or aryl, said aryl being substituted with one or two groups independently selected from NR"$_9$R"$_{10}$, OH, COOR"$_9$, SO$_3$R"$_9$ or OCOR"$_9$; and R"$_7$ and R"$_8$ are each independently H, OH, or taken together is O;

R"$_1$ and R'$_{1a}$ are each independently R"$_6$, with the proviso that at least one of R"$_1$ and R'$_{1a}$ is H.

the method comprising the step of reacting a bisindolylmaleimide compound of the generaly formaul [II]:

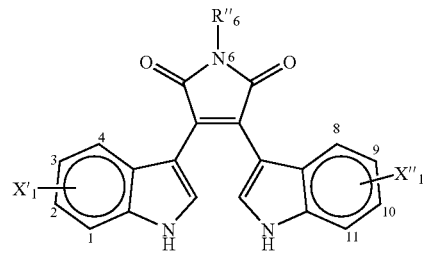

wherein:

$X'_1$, $X''_1$, R"$_6$, R"$_7$ and R"$_8$ are as described above in formula [I], with an oxidizing agent in the presence of an oxygen containing gas at a temperature and for a time sufficient to yield indolopyrrolocarbazole compound of the general formula [I], wherein R"$_7$ and R"$_8$ together are =O and R"$_1$ and R"$_{1a}$ are both H. Optionally, the method includes reducing the indolopyrrolocarbazole compound in the presence of a reducing agent to yield a composition in which R"$_7$ and R"$_8$ are H and/or OH. Optionally, the method further includes substituting the indolopyrrolocarbazole compound such that one of R"$_1$ and R"$_{1a}$ is R"$_6$.

In another aspect of the present invention, there is provided a method for synthesizing a rebeccamycin analog, or a pharmaceutically accpetable salt thereof, of the general formula [III]:

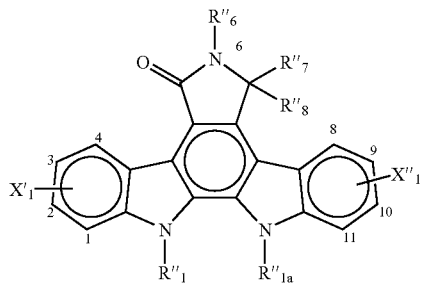

wherein:

R"$_6$ is H, C$_{1-7}$ alkyl, aryl, arylalkyl, OR"$_{10}$, NR"$_9$R"$_{10}$, or OCO(CH$_2$)$_n$NR"$_9$R"$_{10}$, said C$_{1-7}$ alkyl being optionally substituted with one to six of the same or different halogen, NR"$_9$R"$_{10}$, CN, NO$_2$, or aryl, said aryl being substituted with one or two groups independently selected from NR"$_9$R"$_{10}$, OH, COOR"$_9$, SO$_3$R"$_9$ or OCOR"$_9$;

n is an integer of from 0 to 4;

R"$_9$ and R"$_{10}$ are independently H, C$_{1-7}$ alkyl, C$_{1-7}$ cycloalkyl, benzyl, aryl, heteroaryl, any of which groups except H can be substituted with one to six of the same or different halogen, OH, NH$_2$, CN, NO$_2$, —C(=NH)NH$_2$, —CH(=NH), CH(R"$_b$) (CH$_2$)$_n$COOH, CH(R"$_b$) (CH$_2$)$_n$NH$_2$, COOR"$_{12}$, or R"$_9$ and R"$_{10}$ together with the nitrogen atom to which they are attached form a cyclic 5-8 membered non-aromatic ring containing either one or two heteroatoms selected from O, N, or S or R"$_9$ and R"$_{10}$ together form =CHR"$_{11}$R"$_{12}$;

R"$_b$ is H or COOH;

R"$_{11}$ and R"$_{12}$ are independently hydrogen, C$_{1-7}$, alkyl C$_{1-7}$ cycloalkyl, heteroaryl, non-aromatic cyclic 5-8 membered ring containing either one or two heteroatoms selected from O or N, (CH$_2$)$_n$ NR"$_9$R"$_{10}$, (CH$_2$)$_n$OR"$_9$ or (CH$_2$)$_n$COOR"$_9$, said C$_{1-7}$ alkyl being optionally substituted with one to six of the same or different halogen, OH, CN, NO$_2$, aryl or heteroaryl, said aryl or heteroaryl substituted with one or two groups independently selected from NR"$_9$R"$_{10}$, OH, COOR"$_9$, SO$_3$R"$_9$ or OCOR"$_9$;

R"$_7$ and R"$_8$ are independently OH or H, or taken together is O;

independently selected X'$_1$ and X"$_1$ are present at each of the 1-4 and 8-11 positions, respectively, and are selected from H, halogen, OH, —CN, CF$_3$, —COR"$_a$, NO$_2$, OR"$_{11}$, O(CH$_2$)$_n$NR"$_9$R"$_{10}$, O(CH$_2$)$_n$OR"$_9$ and O(CH$_2$)$_n$COOR"$_9$;

R"$_a$ is H, OH, C$_{1-7}$ alkoxy or NR"$_9$R"$_{10}$; and

R"$_1$ and R"$_{1a}$ are each independently R"$_6$, a pentose group (A), or a hexose group (B) of the formulas:

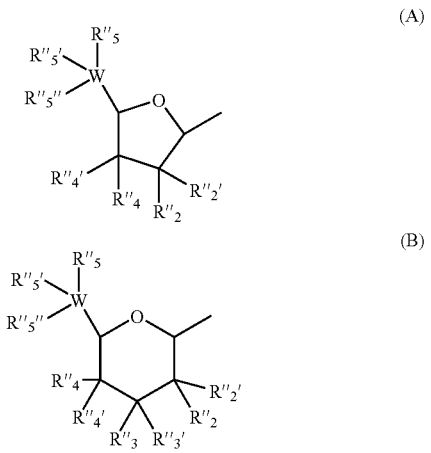

provided that one of R"$_1$ and R"$_{1a}$ is R"$_6$, and the other is (A) or (B), wherein:

R"$_2$, R"$_3$, R"$_4$, R"$_5$ and R"$_{2'}$, R"$_{3'}$, R"$_{4'}$, R"$_{5'}$, and R"$_{5''}$ are each independently H, C$_{1-7}$ alkyl, C$_{1-7}$ cycloalkyl, azido, halogen, NR"$_9$R"$_{10}$, NCH(O)NR"$_9$R"$_{10}$, NHC(O)OR", OR", —C(O)R"$_a$, SR", —OSO$_2$R"$_c$, or together form =N—OH, , =O, =NR"$_{12}$, said C$_{1-7}$ alkyl being optionally substituted with one to six of the same or different halogen, CN, NO$_2$, aryl or heteroaryl, said aryl or heteroaryl being substituted with one or two groups independently selected from NR"$_9$R"$_{10}$, OH, COOR"$_9$, SO$_3$R"$_9$ or OCOR"$_9$;

R"$_c$ is C$_{1-7}$ alkoxy or C$_{1-7}$aryl, which may be substituted or unsubstituted; and W is C or N;

the method including the steps of:

(a) reacting a bisindolylmaleimide compound of the general formula [II];

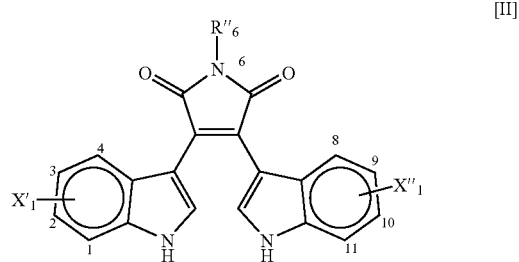

wherein:

R"$_6$, R"$_7$, R"$_8$, X'$_1$, and X"$_1$ are as defined above in formula [I] with an oxidizing agent while sparging with an oxygen containing gas at a temperature and for a time sufficient to yield the indolopyrrolocarbazole compound of the general formula [I]; and (b) glycosylating the indolopyrrolocarbazole compound of the general formula [I] with a sugar moiety selected from a pentose group (A) or a hexose group (B) as defined above, to yield the rebeccamycin compound of the general formula [III], in which one of R"$_1$ or R"$_{1a}$ is a sugar moiety and the other is R"$_6$.

Thus, the process of producing rebeccamycin and its analogs in accordance with the present invention includes:

(a) reacting a bisindolylmaleimide compound of the general formula [II]:

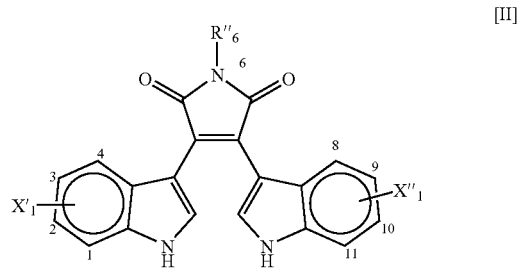

R"$_6$, R"$_7$, R$_8$, X'$_1$ and X"$_1$ are as previously defined, with an oxidizing agent while sparging with an oxygen containing gas at a temperature and for a time sufficient to yield the indolopyrrolocarbazole compound of the general formula [I]:

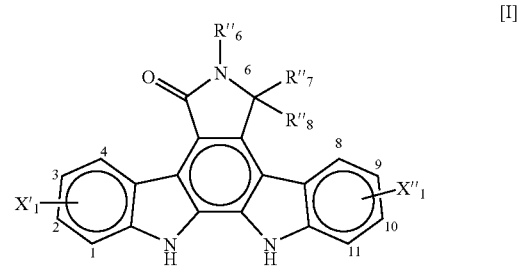

and (b) glycosylating the indolopyrrolocarbazole compound of the general formula [I] with a sugar moiety selected from a pentose group (A) or a hexose group (B) as defined above, to yield the rebeccamycin compound of the general formula [III].

DETAILED DESCRIPTION OF THE INVENTION

The present invention is directed to methods for making indolopyrrolocarbazole ring compounds in an efficient and cost effective manner, and to synthesizing rebeccamycin compounds and analogs thereof using the indolopyrrolocarbazole compounds. As a result, it has now been found that the compounds represented by the general formula [I] may be produced at low cost in relatively large yields and with improved purity.

Methods of Synthesizing Indolopyrrolocarbazole Ring Compounds

For one embodiment of the present invention, the compounds of the general formula [I] can be prepared according to the methods represented by the following Scheme A.

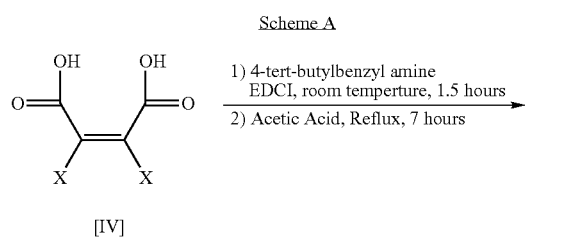

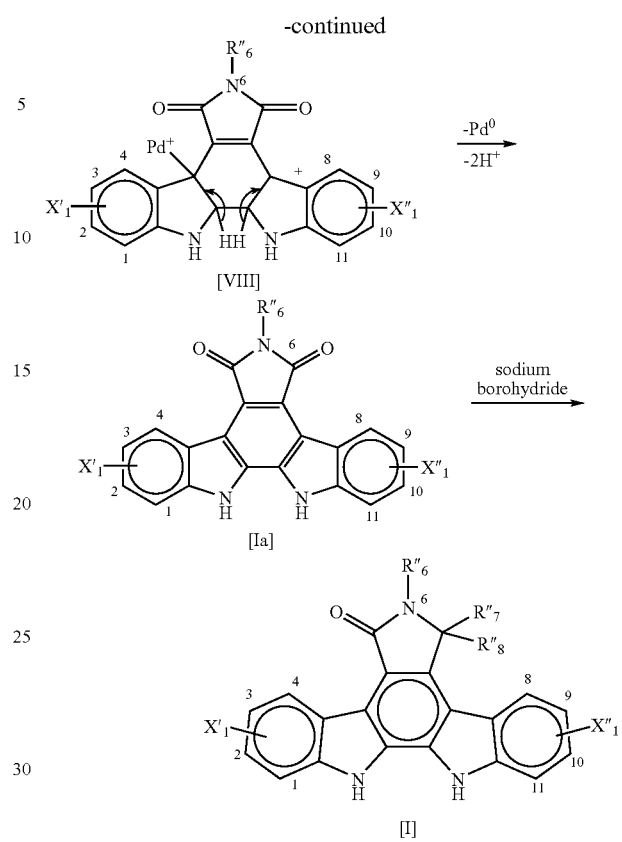

The definitions of the symbols and terms used in scheme A are as follows:

In the general formulas:

$X'_1$ and $X''_1$ are selected from H, halogen, OH, —CN, $CF_3$, —$COR''_a$, $NO_2$, $OR''_{11}$, $O(CH_2)_nNR''_9R''_{10}$, $O(CH_2)_nOR''_9$ and $O(CH_2)_nCOOR''_9$, wherein:

n is an integer of from 0 to 4;

$R''_a$ is H, OH, $C_{1-7}$alkoxy or $NR''_9R''_{10}$;

$R''_9$ and $R''_{10}$ are independently H, $C_{1-7}$alkyl, $C_{1-7}$ cycloalkyl, phenyl, benzyl, aryl, heteroaryl, any of which groups except hydroen can be substituted with one to six of the same or different halogen, OH, $NH_2$, CN, $NO_2$, —C(=NH)$NH_2$, —CH(=NH), CH($R''_b$) $(CH_2)_n$ COOH, CH($R''_b$)$(CH_2)_n$ $NH_2$, $COOR''_{12}$, or $R''_9$ and $R''_{10}$ together with the nitrogen atom to which they are attached form a cyclic 5-8 membered non-aromatic ring containing either one or two heteroatoms selected from O, N, or S or $R''_9$ and $R''_{10}$ together form =CHR''$_{11}$R''$_{12}$;

$R''_b$ is H or COOH;

$R''_{11}$ and $R''_{12}$ are each independently hydrogen, $C_{1-7}$alkyl, $C_{1-7}$cycloalkyl, heteroaryl, non-aromatic cyclic 5-8 membered ring containing either one or two heteroatoms selected from O or N, $(CH_2)_n$ $NR''_9R''_{10}$, $(CH_2)_nOR''_9$ or $(CH_2)_nCOOR''_9$, said $C_{1-7}$alkyl being optionally substituted with one to six of the same or different halogen, OH, CN, $NO_2$, aryl or heteroaryl, said aryl or heteroaryl substituted with one or two groups independently selected from $NR''_9R''_{10}$, OH, $COOR''_9$, $SO_3R''_9$ or $OCOR''_9$;

$R''_6$ is H, $C_{1-7}$alkyl, aryl, arylalkyl, $OR''_{10}$, $NR''_9R''_{10}$, or $OCO(CH_2)_nNR''_9R''_{10}$, said $C_{1-7}$alkyl being optionally substituted with one to six of the same or different halogen, NR"$_9$R"$_{10}$, CN, NO$_2$, aryl, said aryl being substituted with one or two groups independently selected from NR"$_9$R"$_{10}$, OH, COOR"$_9$, SO$_3$R"$_9$ or OCOR"$_9$; and R"$_7$ and R"$_8$ are each independently H, OH, or taken together is O;

R$_5$ is selected from the group consisting of X'$_1$ and X"$_1$.

X represents a leaving group. Examples of a suitable leaving group include halogen atoms (i.e., fluorine, chlorine, bromine and iodient atoms).

Y represents an alkali metal atom such as magnesium.

Z represents a halogen atom (i.e., fluorine, chlorine, bromine and iodine atoms).

The oxidizing agent reacts with a compound of the general formula [III] to produce the indolopyrrolocarbazole compound of the general formula [I]. Preferably, CuCl$_2$ and Pd(OAc)$_2$ are reacted in the presence of an oxygen containing gas. More preferably, the oxygen containing gas is air sparged into the reaction solution.

The reaction shown in Scheme A will now be described. It will be understood that where typical or preferred conditions (i.e., reaction temperature, times, mole ratios of reactants, solvents, pressures, etc.) are given, other process conditions may also be used unless otherwise state. Optimum reaction conditions may vary with the particular reactants or solvent used, and such conditions may be determined by one skilled in the art through known routine optimization procedures.

A compound of the general formula [IV] reacts with an R-substituted amine compound in the presence of 1-(3-dimethylaminopropyl)-3-ethylcarbodiimide hydrochloride (EDCI). Selection of the R-substituted amine compound allows for introduction of an R group on the N at the 6 position of the intermediate of general formula (II). Selection of the amount of EDCI used is usually in the range of 1 to 2 molar equivalents, preferably 1.05 molar equivalents. The reaction mixture is then refluxed in the presence of a weak acid such as acetic acid for a suffient time (i.e. about 7 hours). The resulting product is a maleimide compound of the general formula [V]. The maleimide compound is, for example, N-p-t-butyl protected dibromomaleimide. The reaction is performed in the presence of a solvent. Typical solvents known to those skilled in the art may be used in this reaction.

The reaction temperature may be in the range from about 30° C. to about 180° C. A preferable reaction temperature is from about 60° C. to about 150° C. A more preferable reaction temperature is from about 90° C. to about 110° C.

The reaction of the maleimide compound of the general formula [V] specifically a dihalomaleimide derivative with an R-substituted indole compound of the general formula [VI] such as 5-fluorindole, in the presence of a base such as ethylmagnesium bromide, or the like, in organic solvents like tetrahydrofuran (THF), benzene, or toluene or combinations thereof, yields a bisindolylmaleimide compound of the general formula [III]. The amount of 5-fluoroindole and ethyl-magnesium bromide is usually in the range of about 1-3 molar equivalents each, preferably 2.2 molar equivalents and 2.3 molar equivalents, respectively. The reaction temperature is usually in the range of from about −20° C. to reflux temperature, preferably about 105° C.

A compound of the general formula [I] can be prepared by cyclizing a compound of the general formula [III] in the presence of an oxidizing agent. The reaction can be carried according to the Wacker-type catalytic reaction. See, Tsuji, J, *Synthesis,* 1984, 369. Preferred oxidizing agents include any palladium or copper salt having an oxidation state of 2+. Examples of suitable oxidizing agents include Cu(NO$_3$)$_2$, Cu(OAc)$_2$ and other Cu$^{2+}$ salts and PdCl$_2$, Pd(OOCCF$_3$)$_2$, PdSO$_4$ and other Pd$^{2+}$ salts. More preferably, the oxidizing agents CuCl$_2$ and Pd(OAc)$_2$ are both used in amounts of about 100 mol % and 5 mol %, respectively.

The reaction is performed in the presence of an oxygen containing gas. Preferably, atmospheric air is sparged for providing a steady supply of a stoichiometric oxidant. The oxidant allows for regeneration of spent oxidizing agent.

The bisindolylmaleimide compound thus produced includes two ketones. The bisindolylmaleimide is then further reacted with a reducing agent to obtain the indolylmaleimide compound when R"$_7$ and R"$_8$ are H and/or OH. Typical reducing agents known to those skilled in the art may be used. Examples include sodium borohydride, aluminum hydride or the like.

The reaction is preferably conducted in the presence of a solvent. Examples of useful solvents include, but are not limited to, dimethylformamide (DMF), toluene, dioxane, methyl chloride, toluene, ether and the like. Solvents having boiling points greater than about 80° C. are most appropriate.

The reaction temperature is usually in the range of from about 80° C. to 140° C., preferably 90° C. to 120° C. The reaction time is usually in the range of from about 2 to 18 hours, preferably from about 4 to 16 hours, depending on the moieties occupying R"$_6$, X'$_1$, and X"$_1$ groups. Table 1 provides reaction temperatures, reaction times, and % yields for various bisindolylmaleimide compounds made according to the method of the present invention.

TABLE 1

Reaction Conditions and Expected Yields from the Oxidative Cyclization Reaction corresponding with R"$_6$, X'$_1$ and X"$_1$ groups

| Carbazole Group | R"$_6$ | X'$_1$ | X"$_1$ | Temp. (° C.) | Time (hour) | Isolated Yield (%) |
|---|---|---|---|---|---|---|
| 1 | p-t-Bu-Bn | 1-Cl | 11-Cl | 120 | 12 | 88 |
| 2 | p-t-Bu-Bn | 3-F | 9-F | 120 | 16 | 81 |
| 3 | p-t-Bu-Bn | 3-Br | 9-Br | 120 | 10 | 74 |
| 4 | H | 3-F | 9-F | 120 | 8 | 78 |
| 5 | p-t-Bu-Bn | 2-F; 3-F | 9-F, 10-F | 120 | 16 | 82 |
| 6 | p-t-Bu-Bn | 3-OMe | 9-OMe | 90 | 4 | 86 |
| 7 | p-t-Bu-Bn | 3-F | 9-F | 90 | 8 | 79 |
| 8 | t-Bu | 3-F | 9-F | 90 | 6 | 62 |
| 9 | DMB | 3-F | 9-F | 90 | 5 | 58 |

Bu: Butyl
Bn: Benzyl
DMB: dimethoxyl benzyl

During the oxidative cyclization reaction, the ring system of the bisindolylmaleimide compound of the general formula [III] undergoes a change in electron density towards an electron rich environment which facilitates the formation of a complex compound of the general formula [VII]. Eventually, a stabilized cation intermediate compound of the general formula [VIII] is formed which is believed to be a turnover limiting step. The oxidative cyclization reaction yields the desired indolo[2,3-a]pyrrolo[3,4-c]carbazole compound of the general formual [I], having two ketone groups. This is the preferred form of the indolopymolocarbazole compound for use in synthesizing rebeccamycin analogs. However, further reducing one of the ketones is also within the scope of the invention.

The oxidative cyclization of bisindolylmaleimide compounds of the general formula [II] facilitated by a Wacker-type catalytic system provides a general and practical approach for the preparation of rebeccamycin aglycone and related analogs in a cost-effective and simple process.

Advantageously, the regeneration of cupric chloride ($CuCl_2$) and palladium diacetate ($Pd(OAc)_2$) is achieved using processes known to those skilled in the art. See Tsuji, *J. Synthesis* 1984, 369, herein incorporated by reference. The regeneration can be summarized as follows:

$$Pd^0 + 2CuCl_2 + 2HOAc \rightarrow Pd(OAc)_2 + 2CuCl + 2HCl$$
$$4CuCl + O_2 + 4HCl \rightarrow 4CuCl_2 + 2H_2O$$

Regeneration of precious catalyst is a significant development in synthesis of the indolopyrrolocarbazole compounds. In contrast to prior art methods, which require a large excess of $Pd^{2+}$ or $Cu^{2+}$ catalyst (i.e., about 250 mol %), the present process utilizes oxygen, for example from sparged air, to provide a catalytic cycle of sequential oxidation and reduction reactions to convert $Pd^0$ and/or $Cu^0$ that has been used in the process back to $Pd^{2+}$ and/or $Cu^{2+}$ As a result, only about 5 mol % for Pd, and 100 mol % for Cu, is required in the present process. The results obtained using the method of the present invention represent a significant improvement in yield (about 80%) as compared to that obtained using prior art methods (about 40%). See, for example, *Tetrahedron Letters* 42: 3271-3273 (2001). Furthermore, the indolopyrrolocarbazole compounds obtained in the present method are more readily isolated and purified as compared to those obtained using prior art methods.

Preferred indolylmaleimide compounds useful as rebeccamycin intermediates include those having two ketone groups, with $R''_6$ being H, or $-(CH_2)_4-$ and $X'_1$ and $X''_1$ being either Cl in the 1- and 11-position or F in the 3- and 9-positions.

EXAMPLE 1

Synthesis of an Indolopyrrolocarbazole Compound of the General Formula [I]

($R'_6$=p-tert-butylbenzyl, $X'_1$=3-F, and $X''_1$=9-F)

A synthesis procedure for making an indolopyrrolocarbazole compound of the general formula [I] wherein $R''_6$=p-tert-butylbenzyl, $X'_1$=3-F, and $X''_1$=9-F, was performed.

1.0 gram of a bisindolylmaleimide compound of the general formula [II], wherein $R''_6$=p-tert-butylbenzyl, $X'_1$=3-F, and $X''_1$=9-F, (1.96 mmol) was charged to a 50 mL, 3-neck flask equipped with a condenser and a thermocouple along with 22 mg of palladium diacetate ($Pd(OAC)_2$, 0.0982 mmol) and 15 mL of DMF to yield a reddish-brown solution. The solution was stirred at ambient temperature for about 10 minutes. 0.26 g of cupric chloride (1.96 mmol) was added portion by portion over 5 minutes. Air was sparged into the resulting suspension. The suspension was heated in an oil bath while being stirred for 16 hours. The oil bath temperature was maintained at about 125° C. with an internal temperature of about 120° C. The reaction progress was monitored by high pressure liquid chromatography. During this period, a greenish-yellow solid was precipitated from the suspension. The suspension was cooled to a temperature of about 5° C. with an ice-water bath, and 10 mL of water was added slowly over a period of 10 minutes. The resulting brownish suspension was maintained at a temperature of about 5° C. for 4 hours. The suspension was then filtered through a sintered glass funnel (type C) and was twice washed with 1 mL of water, to yield 1.7 grams of a crude product in the form of a brown solid. The crude product was recovered through recrystallization using 20 mL of N-methyl-2-pyrrolodinone and 1 mL of water. The recrystallization process yielded 0.81 g of the indolopyrrolocarbazole compound of the general formula [I] ($R''_6$=p-tert-butylbenzyl, $X'_1$=3-F, and $W''_1$=11-F) in the form of a greenish-yellow solid to provide a yield of about 81% (HPLC, AP 98).

MS: $(M+H)^+$ 541; $^1$H-NMR (400 MHz, DMSO-$d_6$): δ11.75 (s, 2H, N-H), 8.84 (d, J=7.8, 2H), 7.95 (s, 2H), 7.65 (d, J=7.8, 2H), 7.40-7.33 (m, 4H), 4.81 (s,2H), 1.23 (s, 9H); $^{13}$C-NMR (100 MHz, DMSO-$d_6$): 168.7, 162.9, 149.6, 137.4, 134.5, 128.8, 127.9, 125.9, 124.9, 123.4, 120.9, 119.9, 116.4, 116.2, 41.0, 31.3169.1, 154.4, 149.3, 135.3, 134.9, 29.6, 127.5(2C), 124.9(2C), 122.8, 119.1, 116.4, 111.5, 106.4, 55.3, 40.9, 31.3.

Methods of Synthesizing Rebeccamycin Compounds

The present invention provides a novel method for preparing rebeccamycin compounds of the general formula [III] utilizing the indolopyrrolocarbazole compounds of the general formula [I] as synthesized by the above described method of Scheme A according to the following Scheme B:

It will be understood that where typical or preferred conditions (i.e., reaction temperature, times, mole ratios of reactants, solvents, pressures, etc.) are given, other process conditions may also be used unless otherwise stated. Optimum reaction conditions may vary with the particular reactants or solvent used, and such conditions may be determined by one skilled in the art through known routine optimization procedures.

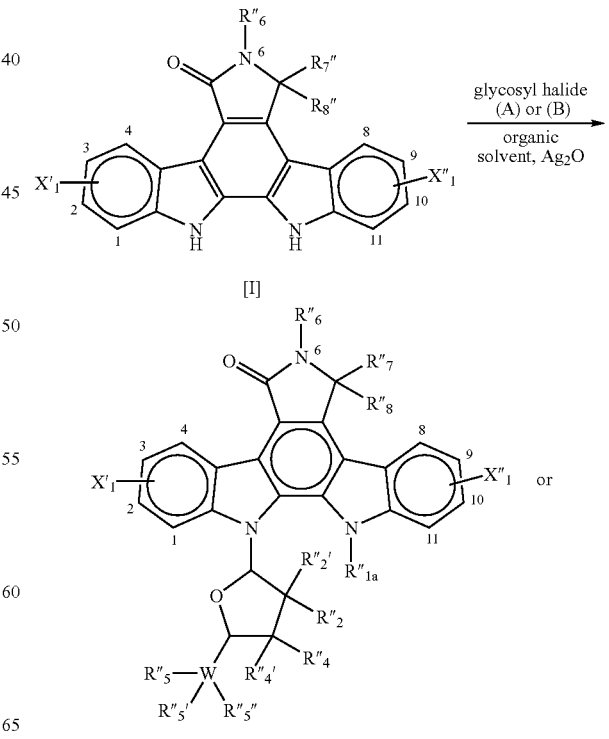

Scheme B

-continued
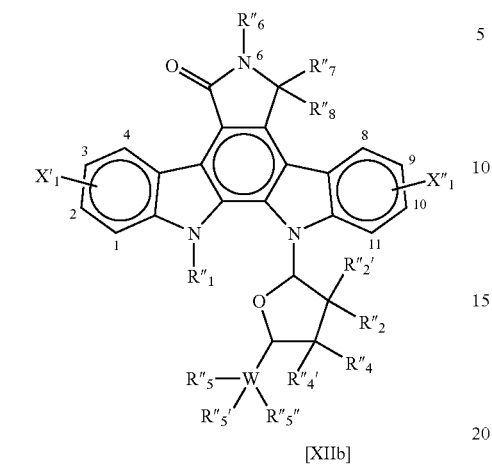
[XIIb]
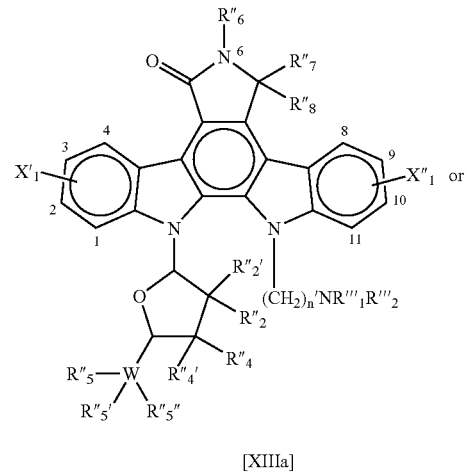
[XIIIa]
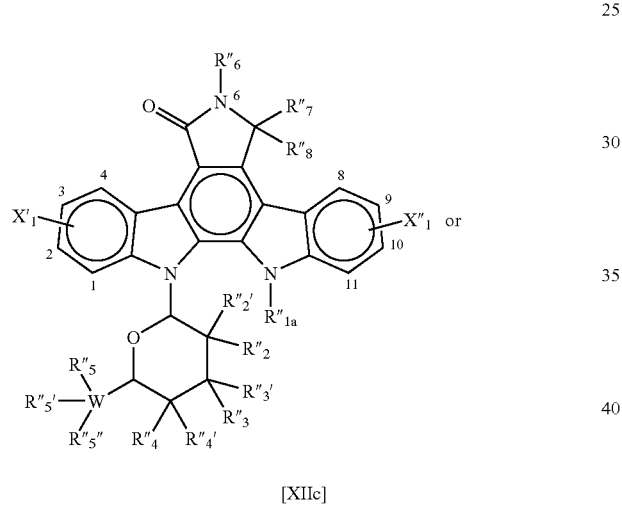
[XIIc]
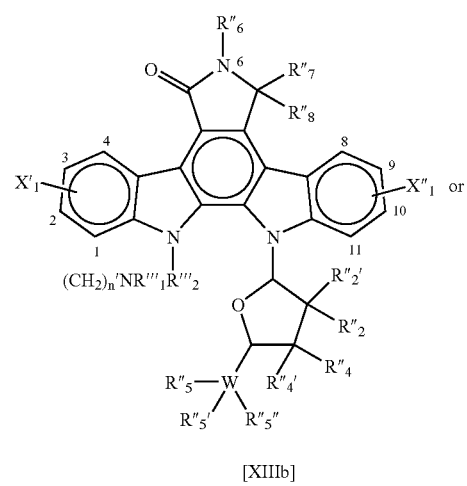
[XIIIb]
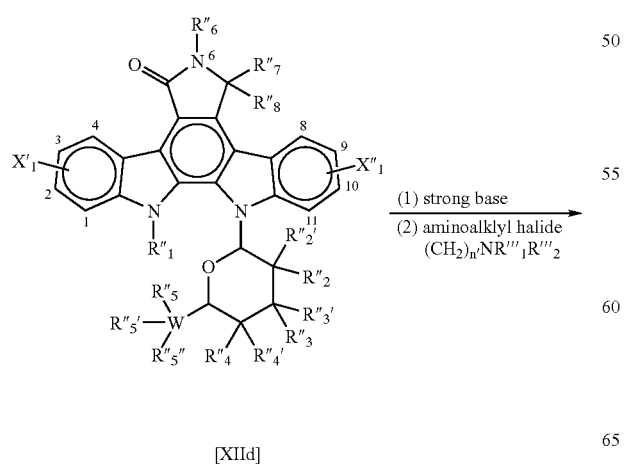
[XIId]
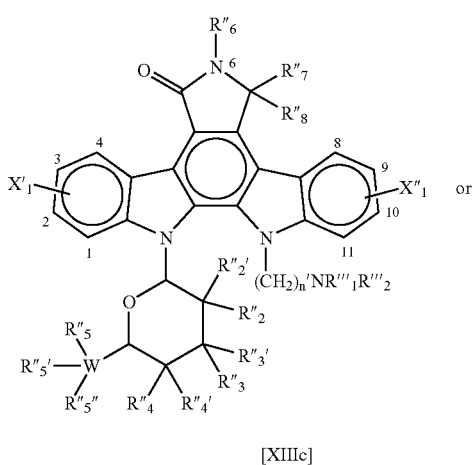
[XIIIc]

-continued

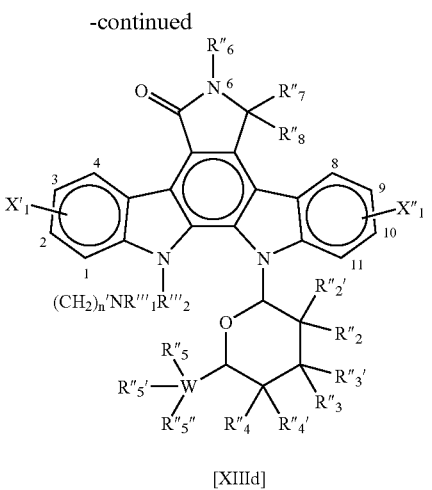

[XIIId]

The definitions of the symbols and terms used in Scheme B are as follows:

$X''_1$, $X''_2$, $R''_6$, $R''_7$ and $R''_8$ are as described previoiusly, (A) represents a pentose group,

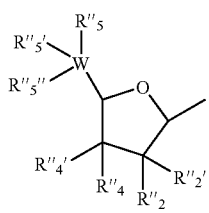

(A)

(B) represents a hexose group,

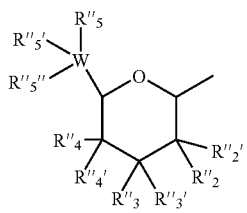

(B)

wherein $R''_2$, $R''_3$, $R''_4$, $R''_5$ and $R''_{2'}$, $R''_{3'}$, $R''_{4'}$, $R''_{5''}$ and $R''_{5'}$ are each independently H, $C_{1-7}$alkyl, $C_{1-7}$cycloalkyl, azido, halogen, $NR''_9R''_{10}$, $NHC(O)NR''_9R''_{10}$, $NHC(O)OR''$, $OR''$, —$C(O)R''_a$, $SR''$, —$OSO_2R''_c$, or together form =N—OH, =O, =$NR''_{12}$, said $C_{1-7}$ alkyl being optionally substituted with one to six of the same of different halogen, CN, $NO_2$, aryl or heteroaryl, said aryl or heteroaryl being substituted with one or two groups independently selected from $NR''_9R''_{10}$, OH, $COOR''_9$, $SO_3R''_9$ or $OCOR''_9$;

$R''_c$ is $C_{1-7}$ alkoxy or $C_{1-7}$ aryl, which may be substituted or unsubstituted; and W is C or N.

Examples of suitable sugar moieties include the 1,2-epoxide described in publications *J. Org. Chem.* 1993, 58, 343-349 and those disclosed in *J. American Chemcial Society* (1989), 111, 6661-6666 and *J. Carbohydrate Chemistry* (1995), 1279-94.

The glycosylation step includes coupling a pentose or hexose moiety in the presence of $Ag_2O$ to yield a N-glycoside rebeccamycin analog.

The rebeccamycin derivative so formed is dissolved in a suitable inert solvent, (i.e. DMF, DMSO or the like) and is reacted sequentially with a strong base, such as KH, $KNH_2$, NaH $H_2$ NaH or the like, followed by an aminoalkyl halide having the desired R-group to form the rebeccamycin compound having an R-group substituent at the 12- or 13-position that is not occupied by the sugar moiety. Any strong base that is compatible with the starting material and solvent may be used. Using strong base, for example NaH, in a relatively large excess amount such as an amount slightly in excess of two-times the molar equivalent of the amount starting material, for example, in the range of about 15% to about 25% and preferably about 20% (18-22%) excess, followed by treatment with an appropriate aminoalkyl compound in an amount about the molar equivalent of starting material, there may be obtained a compound according to the invention having an aminoalkyl substituent on the N-atom in the 12- or 13-position of the rebeccamycin ring system.

When more than two equivalents of base are used, a dianion at N6 and N13 is formed. Since the N13 anion is more reactive than the N6 anion, a N13 aminoalkyl derivative is obtained when only one equivalent of aminoalkyl halide is used. When two equivalents of aminoalkyl halide is used, a N6,N13-diaminoalkyl derivative may be obtained.

Following the reaction of the formula XII compounds with a strong base, the resulting reactive intermediate is reacted in situ with an appropriate reactive aminoalkyl compound by adding the aminoalkyl compound to the mixture of starting material and strong base and intermediate reaction product thereof in inert solvent. Any aminoalkyl compound that is compatible with the starting material and product and solvent may be used, for example, an aminoalkyl halide or sulfonate and the like.

Generally, the reaction of strong base with starting material may be carried-out advantageously at about room temperature, that is, at about 18° C. to about 22° C. The mixture of staring material and strong base, generally, may be stirred for a period of a few minutes to several hours; however, the reaction is usually complete in about 20-30 minutes.

Then, there is added to the stirred mixture of starting material and strong base and resulting reactive intermediate reaction product thereof in inert solvent the appropriate aminoalkyl compound and the resulting mixture may be stirred at room temperataure for about 20-24 hours or at about 4° C. for a shorter period of time, for example, six hours until the reaction of the reactive intermediate with aminoalkyl compound is complete.

It is also possible to introduce an R-group aat the 6 position. Using strong base, for example NaH, in an amount slightly in excess of the molar equivalent of the amount of starting material, for example in the range of from about 5% to about 15% and preferably about 10% (9-11%) excess, followed by treatment with at least one molar equivalent based on rebeccamycin starting material of an appropriate aminoalkyl compound, there may be obtained a compound according to the invention having an aminoalkyl substituent on the N-atom in the 6-position of the rebeccamycin ring system.

Thus, reaction of the rebeccamycin derivative first with a strong base, followed by an aminoalkly provides analogs substituted at the 12- or 13- position not occupied by the sugar moiety. Addition of an R group at the N6 position is also possible.

An alternative method of adding a sugar moiety to the indolylmaleimide comound of formula [II] to the rebeccamycin compounds of the general formula [III] is illustrated, by way of example, in the reaction route of Scheme C wherein a rebeccamycin compound of the general formula [IIIa] is produced.

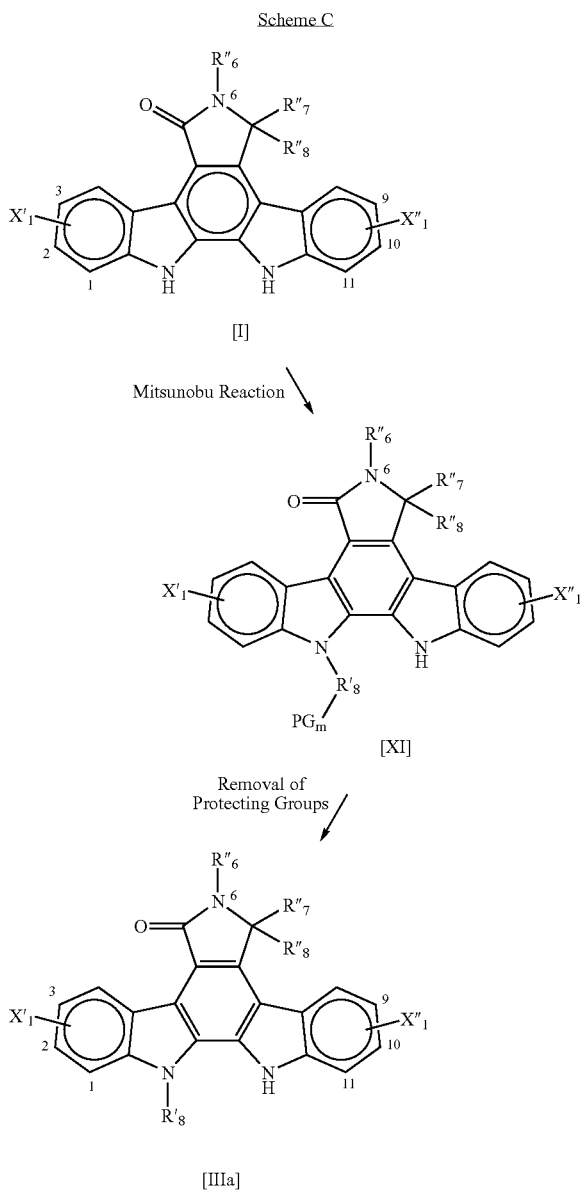

[IIIa]

wherein $R''_6$, $R''_7$, $R''_8$, $X'_1$, $X''_1$, R as defined previously, and $R_8'$ is a pentose (A) or hexose (B) sugar moiety.

PG is a synthetic organic "protecting group" of the type generally used to "protect" a hydroxyl functionality e.g. an acyl type group such as an acetyl, a trifluoroacetyl, or an arylalkyl group like a benzyl or the like, and "m" is any integer. Suitable protecting or blocking groups used in organic synthesis are well known to the practitioner and are adequately described in the appropriate literature. See, e.g., Theodora Greene, *Protective Groups in Organic Synthesis*, John Wile and Sons, New York.

The starting material is an indolopyrrolocarbazole compound of the general formula [I] made by the method of present invention described above. Glycosylation of [I] with a reactive sugar moiety selected from a pentose group (A) or a hexose group (B), in the presence of an appropriate base such as diisopropylethyl amine, hexamethyldisilazide and an organic solvent such as THF, DMF, dioxane, benzene, or dimethoxy ethane (DME) to form the mono- or di- or tri-anion of the indolopyrrolocarbazole compound of formula [I], yields a derivative compound of the general formula [XI].

The glycosylation is achieved by reacting the sugar moiety with the indolopyrrolocarbazole compound of the general formula [I] procedure with an organic phosphene and an azodicarboxylic acid derivative using the well known Mitsunobu reaction in the presence of an ethereal solvent like THF or a chlorinated solvent like $CH_2Cl_2$. The reaction forms a glycosidic linkage between the sugar moiety and the indolopyrrolocarbazole ring by using the organic phosphine, such as triphenylphosphine or tributylphosphine, and the azodicarboxylic acid derivative such as azodicarboxylic acid diethyl ester, azodicarboxylic acid di-tert-butyl ester, azodicarboxylic acid diisopropyl ester, azodicarboxylic acid di-N,N-dimethylamide or azodicarboxylic acid di-N-methylpiperazinamide (See *Synthesis*, I, 1981, pp. 1-28).

The compound of the general formula [XI] is a protected form of the rebeccamycin compound of the general formula [IIIa]. The deprotection of the compound of the general formula [XI] is preferably carried out under conditions which permit selective deprotection such as under acidic conditions or by well known common hydrogenation reaction or the like as shown to one of ordinary skill in the art. Once the removal of the protecting groups is achieved, the compound [IIIa] is yielded. After completion of the reaction, the desired product can be isolated and purified according to techniques widely known in the field of organic chemistry (e.g. precipitation, solvent extraction, recrystallization, and chromatography).

Therefore, the present invention relates to synthesis of rebeccamycin compounds of the general formula [III], as described and defined above, comprising the steps of:

(a) reacting a bisindolylmaleimide compound of the general formula [II]:

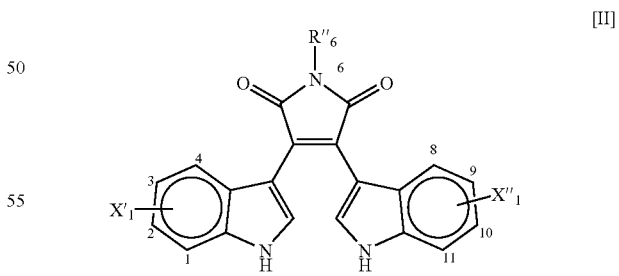

[II]

wherein:

independently selected $X'_1$ and $X''_1$ are at each of the 1-4 and 8-11 positions, respectively, and are selected from H, halogen, OH, —CN, $CF_3$, —$COR''_a$, $NO_2$, $OR''$, $O(CH_2)_n NR''_9 R''_{10}$, $O(CH_2)_n OR''_9$ and $O(CH_2)_n COOR''_9$;

n is an integer of from 0 to 4;

$R''_a$ is H, OH, $C_{1-7}$alkoxy or $NR''_9 R''_{10}$;

R"$_9$ and R"$_{10}$ are independently H, C$_{1-7}$alkyl, C$_{1-7}$cycloalkyl, benzyl, aryl, heteroaryl, any of which groups except hydrogen can be substituted with one to six of the same or different halogen, OH, NH$_2$, CN, NO$_2$, —C(=NH)NH$_2$, —CH(=NH), CH(R"$_b$) (CH$_2$)$_n$ COOH, CH(R"$_b$)(CH$_2$)$_n$ NH$_2$, COOR"$_{12}$, or R"$_9$ and R"$_{10}$ together with the nitrogen atom to which they are attached form a cyclic 5-8 membered non-armatic ring containing either one or two heteroatoms selected from O, N, or S or R"$_9$ and R"$_{10}$ together form =CHR"$_{11}$R"$_{12}$;

R"$_b$ is H or COOH;

R"$_{11}$ and R"$_{12}$ are each independently hydrogen, C$_{1-7}$alkyl, C$_{1-7}$cycloalkyl, heteroaryl, non-aromatic cyclic 5-8 membered ring containing either one or two heteroatoms selected from O or N, (CH$_2$)$_n$ NR"$_9$R"$_{10}$, (CH$_2$)$_n$OR"$_9$ or (CH$_2$)$_n$COOR"$_9$, said C$_{1-7}$alkyl being optionally substituted with one to six of the same or different halogen, OH, CN, NO$_2$, aryl or heteroaryl, said aryl or heteroaryl substituted with one or two groups independently selected from NR"$_9$R"$_{10}$, OH, COOR"$_9$, SO$_3$R"$_9$ or OCOR"$_9$;

R"$_6$ is H, C$_{1-7}$alkyl, aryl, arylalkyl, OR"$_{10}$, NR"$_9$R"$_{10}$, or OCO(CH$_2$)$_n$NR"$_9$R"$_{10}$, said C$_{1-7}$alkyl being optionally substituted with one to six of the same or different halogen, NR"$_9$R"$_{10}$, CN, NO$_2$, aryl, said aryl being substituted with one or two groups independently selected from NR"$_9$R"$_{10}$, OH, COOR"$_9$, SO$_3$R"$_9$ or OCOR"$_9$; and R"$_7$ and R"$_8$ are each independently H, OH, or taken together is O, with an oxidizing agent in the presence of oxygen gas at a temperature and for a time sufficient to yield the indolopyrrolocarbazole compound of the general formula [I]:

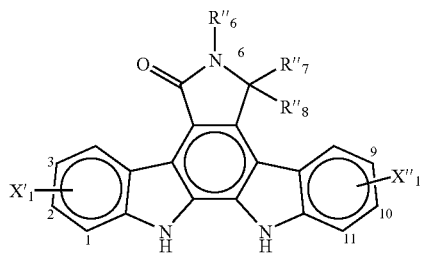

[I]

wherein X"$_1$, X"$_1$, R"$_6$, R"$_9$ and R"$_8$ are as defined above in formula [II], and (b) glycosylating the indolopyrrolocarbazole compound of the general formula [I] at one of positions 12- and 13-, with a sugar moiety selected from a pentose group (A) or a hexose (B) group:

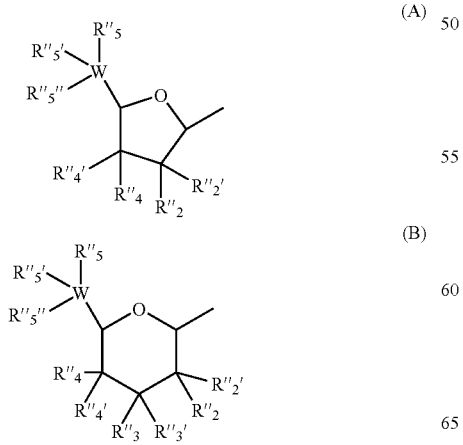

(A)

(B)

wherein:

R"$_2$, R"$_3$, R"$_4$, R"$_5$ and R"$_{2'}$, R"$_{3'}$, R"$_{4'}$, R"$_{5''}$ and R"$_{5'}$ are each independently H, C$_{1-7}$ alkyl, C$_{1-7}$ cycloalkyl, azido, halogen, NR"$_9$R"$_{10}$, NHC(O)NR"$_9$R"$_{10}$, NHC(O)OR", OR", —C(O)R"$_a$, SR", —OSO$_2$R"$_d$, or together form =N—OH, , =O, =NR"$_{12}$, said C$_{1-7}$ alkyl being optionally substituted with one to six of the same or different halogen, CN, NO$_2$, aryl or heteroaryl, said aryl or heteroaryl being substituted with one or two groups independently selected from NR"$_9$R"$_{10}$, OH, COOR"$_9$, SO$_3$R"$_9$ or OCOR"$_9$; to yield the rebeccamycin compound of the general formula [III].

In a preferred embodiment, the invention comprises the method of synthesizing a rebeccamycin compound of formula [III], as described above, wherein the formula [III] compound is selected from the group consisting of:

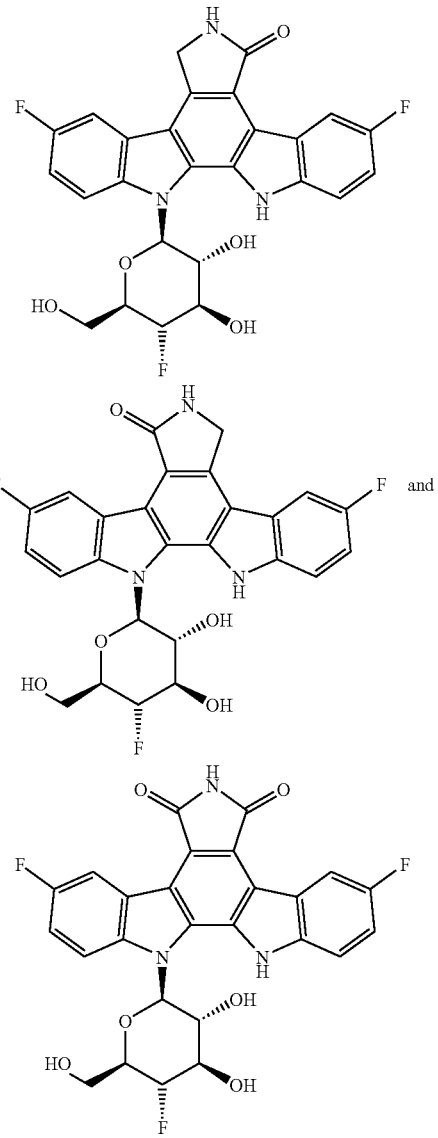

It is possible to provide rebeccamycin compounds that are substituted at one or more of the 6-position and the 12- or 13-position not occupied by a sugar moiety. As has been previously described, it is possible to use an intermediate already substituted at the 6-position. In this case, no further reaction is necessary to include the appropriate R group at the 6-position. Alternatively, an intermediate in which H is at the 6-position may be used, and the rebeccamycin analog further substituted after addition of the sugar moiety. It is also possible to use an intermediate already substituted at the 12- or 13-position to form the rebeccamycin analog. However, this is disfavored due to difficulty in adding the sugar moiety due to steric hinderance of the binding site. Therefore, if a substitution at the 12- or 13-position not occupied by the sugar moiety is desired, it is preferable to perform the substitution step after the sugar moiety has been attached to the rebeccamycin analog.

Thus, the invention comprises a method of synthesizing a rebeccamycin compound and pharmaceutically acceptable acid addition and base salts thereof, having the general formula [X]:

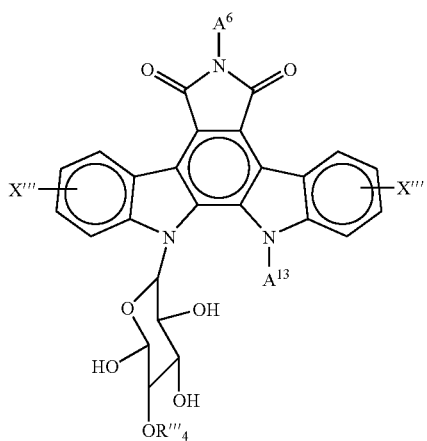

$A^6$ and $A_{13}$ are selected from H and $-(CH_2)_{n'}NR'''_1R'''_2$ and at least one of $A^6$ and $A^{13}$ is $-(CH_2)_{n'}NR'''_1R'''_2$;

n' is an integer from 1 to 6;

$R'''_1$ and $R'''_2$, independently, are selected from H, unsubstituted and substituted $C_1$-$C_6$ alkyl, aralkyl having 1 to 3 carbons in the alkyl moiety and unsubstituted phenyl or phenyl substituted with 1 to 3 alkyl, alkoxy, hydroxy, halo, carboxyl, alkoxycarbonyl, and amino and mono- and di-lower-alkylamino groups in the aryl moiety, and aryl selected from unsubstituted phenyl and phenyl substituted with 1 to 3 alkyl, alkoxy, hydroxy, halo, amino, mono- and dialkylamino, nitro, carboxyl, alkoxycarbonyl, and cyano groups, provided that both $R'''_1$ and $R'''_2$ are not each aryl and, when taken together, $R'''_1$ and $R'''_2$ may be selected from $-(CH_2)_4-$ and $(CH_2)_2-R'''_3-(CH_2)_2-$ to form a 5- or 6 membered ring together with the N-atom, wherein $R'''_3$ is selected from $CH_2$, NH, O and S;

X''' is selected from H, F, Cl, Br, $C_1$-$C_3$ alkyl, OH, carboxy, alkoxycarbonyl and alkoxy wherein the alkyl moiety is $C_1$-$C_3$ alkyl, benzyloxy, amino, and mono- and dialkylamino; and $R'''_4$ is selected from H and $CH_3$, the method comprising the steps of:

(a) reacting a bisindolyl-maleimide compound of the general formula [II]:

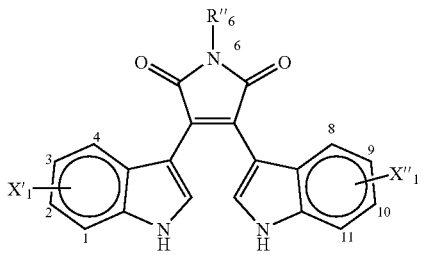

wherein:

$X'_1$ and $X''_1$ are $X'''_1$, and $R''_6$ is $A^6$, with an oxidizing agent in the presence of an oxygen containing gas at a temperature and for a time sufficient to yield the indolopyrrolocarbazole compound of formula [X] wherein $A^{13}$ is H;

(b) glycosylating the indolopyrrolocarbazole compound of the general formula [I] wherein $X'_1$, $X''_1$, $R''_6$, $R''_7$ and $R''_8$ are as defined in formula [II] at one of positions 12- and 13-, with a sugar moiety selected from a pentose group (A) or a hexose (B);

(c) deprotecting the sugar moiety using base hydrolysis; and (d) substituting said position 12- or 13- not occupied by a sugar moiety with an R group $(CH_2-)_{n'}-NR'''_1R'''_2$, wherein n', $R'''_1$ and $R'''_2$ are as defined above in formula [X], by reaction with an amine halide including said R group, to yield the formula [I] compound wherein $A^{13}$ is $-(CH_2-)_{n'}NR'''_1R'''_2$.

Compounds of the general formula [X], pharmaceutical compositions containing formula [X] compounds, and methods to make such compounds and compositions are fully described in U.S. Pat. No. 4,785,085, U.S. Pat. No. 4,808,613 and U.S. Pat. No. 5,496,809, all of which are herein incorporated by reference.

In a preferred embodiment, the invention comprises a method of synthesizing a rebeccamycin compound of the general formula [X], or pharmaceutically acceptable acid addition and base salts thereof, as described above, wherein the formula [X] compound is:

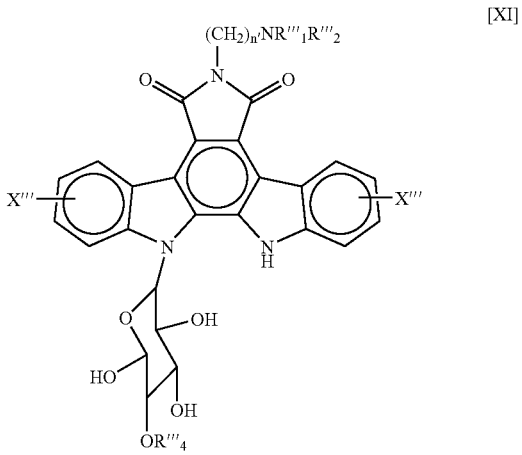

wherein:

X''' is selected from H, F, Cl, Br, $C_1$-$C_3$ alkyl, OH, carboxyl, alkoxycarbonyl and alkoxy wherein the alkyl moiety is $C_1$-$C_3$ alkyl, benzyloxy, amino, and mono- and dialkylamino;

n' is an integer from 1 to 6;

$R'''_1$ and $R'''_2$, independently, are selected from H, unsubstituted and substituted $C_1$-$C_6$ alkyl, aralkyl having 1 to 3 carbons in the alkyl moiety and unsubstituted phenyl or phenyl substituted with 1 to 3 alkyl, alkoxy, hydroxy, halo, carboxyl, alkoxycarbonyl, and amino and mono- and di-lower-alkylamino groups in the aryl moiety, and aryl selected from unsubstituted phenyl and phenyl substituted with 1 to 3 alkyl, alkoxy, hydroxy, halo, amino, mono- and dialkylamino, nitro, carboxyl, alkoxycarbonyl, and cyano groups provided that both $R'''_1$ and $R'''_2$ are not each aryl and, when taken together, $R'''_1$ and $R'''_2$ may be selected from —($CH_2$—)$_4$— and ($CH_2$)$_2$—$R'''_3$—($CH_2$)$_2$— to form a 5- or 6 membered ring together with the N-atom, wherein $R'''_3$ is selected from $CH_2$, NH,O and S; and $R'''_4$ is selected from H and $CH_3$.

In another preferred embodiment, the invention comprises a method of synthesizing a rebeccamycin compound of the general formula [X] or [XI], or a pharmaceutically acceptable salt thereof, as described above, wherein X''' is selected from H, Cl, Br, OH, $OCH_3$ and $OCH_2C_6H_5$.

In yet another preferred embodiment, the invention comprises a method of synthesizing a rebeccamycin compound of the general formula [I] or [XI], or a pharmaceutically acceptable salt thereof, as described above, wherein n' is selected from the integers 1, 2, and 3; and $R'''_1$ and $R'''_2$, are independently selected from H, $C_1$-$C_3$ alkyl, and —($CH_2$)$_4$—.

In still yet another preferred embodiment, the invention comprises a method of synthesizing a rebeccamycin compound of the general formula [X], or a pharmaceutically acceptable salt thereof, as described above, wherein X''' is Cl in each of the 1- and 11-positions. In another embodiment n' is an integer selected from 2 and 3; and $R'''_1$ and $R'''_2$ are each $C_2H_5$.

In still yet another preferred embodiment, the formula [X] compound is:

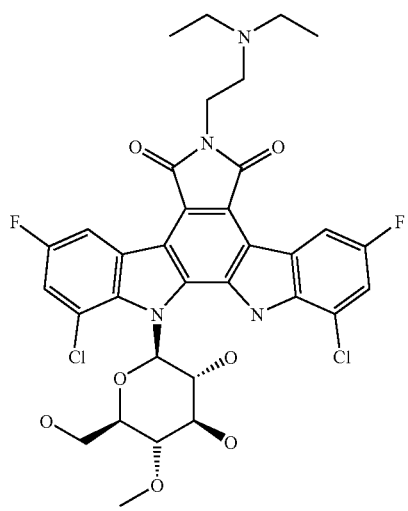

The rebeccamycin compounds of the general formulas [III] and [X] can exist in the form of pharmaceutically acceptable salts. Such salts include addition salts with inorganic acids such as, for example, hydrochloric acid and sulfuric acid, and with organic acids such as, for example, acetic acid, citric acid, methanesulfonic acid, toluene sulfonic acid, tartaric acid, and maleic acid. Further, in case the compounds of the general formula [III] of this invention contain an acidic group, the acidic group can exist in the form of alkali metal salts such as, for example, a potassium salt and a sodium salt; alkaline earth metal salts such as, for example, a magnesium salt and a calcium salt; and salts with organic bases such as ethylammonium salt and an arginine salt.

The indolopyrrolocarbazole compounds of the general formula [I] prepared by the above-described method of the present invention may be used as starting materials for synthesizing rebeccamycin compounds of the general formula [III]. It will be understood that where typical or preferred conditions (i.e. reaction temperature, times, mole ratios of reactants, solvents, pressures, etc.) are given, other process conditions may also be used unless otherwise stated. Optimum reaction conditions may vary with the particular reactants or solvent used, but such conditions may be determined by one skilled in the art through known routine optimization procedures.

The indolopyrrolocarbazole compound of the general formula [I] may coupled to a sugar moiety selected from a pentose group (A) or a hexose group (B) and the like in the presence of $Ag_2O$ to yield the rebeccamycin compound of the general formula [III] or via the Mitsunobu reaction. Protected sugar moieties may be deprotected.

The rebeccamycin compounds of the generl formula [III] can be further modified using methods disclosed herein using indolopyrrolocarbazole compounds of the general formula [I] as intermediates. Methods of synthesizing rebeccamycin compounds and analogs of the general formulae [I] and [III] are further disclosed in U.S. Pat. No. 4,785,085, PCT International Publication No. WO 98/07433, and copending U.S. Patent Application Ser. No. 60/278043, all of which are herein incorporated by reference.

It is understood that the procedure for synthesizing rebeccamycin compounds of the general formula [III] is not limited to the those disclosed herein, but may include any known synthesis methods which require the supply of indolopyrrolocarbazole compounds of the general formula [II] as starting materials.

What is claimed is:

1. A method for making an indolopyrrolocarbazole compound according to general formula [I]:

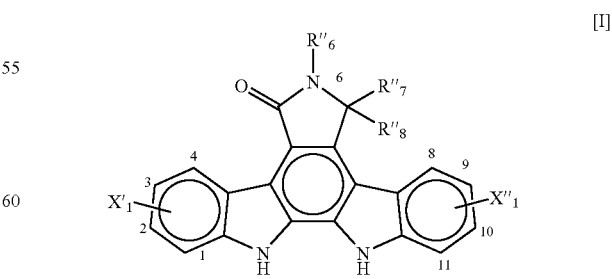

wherein:
independently selected $X'_1$ and $X''_1$ are at each of the 1-4 and 8-11 positions, respectively, and are selected from H, halogen, OH, —CN, CF$_3$, —COR'$_a$, NO$_2$, OR", O(CH$_2$)$_n$NR'$_9$R"$_{10}$, O(CH$_2$)$_n$OR"$_9$ and O(CH$_2$)$_n$COOR"$_9$;

n is an integer of from 0 to 4;

R"$_a$ is H, OH, C$_{1-7}$alkoxy or NR"$_9$R"$_{10}$;

R"$_9$ and R"$_{10}$ are independently H, C$_{1-7}$alkyl, C$_{1-7}$cycloalkyl, phenyl, benzyl, aryl, heteroaryl, any of which groups except hydrogen can be substituted with one to six of the same or different halogen, OH, NH$_2$, CN, NO$_2$, —C(=NH)NH$_2$, —CH(=NH), CH(R'$_b$) (CH$_2$)$_n$COOH, CH(R'$_b$)(CH$_2$)$_n$ NH$_2$, COOR"$_{12}$, or R"$_9$ and R"$_{10}$ together with the nitrogen atom to which they are attached form a cyclic 5-8 membered non-aromatic ring containing either one or two heteroatoms selected from O, N, or S or R"$_9$ and R"$_{10}$ together form =CHR"$_{11}$R"$_{12}$;

R"$_b$ is H or COOH;

R"$_{11}$ and R"$_{12}$ are each independently hydrogen, C$_{1-7}$alkyl, C$_{1-7}$cycloalkyl, heteroaryl, non-aromatic cyclic 5-8 membered ring containing either one or two heteroatoms selected from O, or N, (CH$_2$)$_n$ NR"$_9$R"$_{10}$, (CH$_2$)$_n$OR"$_9$ or (CH$_2$)$_n$COOR"$_9$, said C$_{1-7}$ alkyl being optionally substituted with one to six of the same or different halogen, OH, CN, NO$_2$, aryl or heteroaryl, said aryl or heteroaryl substituted with one or two groups independently selected from NR"$_9$R"$_{10}$, OH, COOR"$_9$, SO$_3$R"$_9$ or OCOR"$_9$;

R"$_6$ is H, C$_{1-7}$alkyl, aryl, arylalkyl, OR"$_{10}$, NR"$_9$R"$_{10}$, or OCO(CH$_2$)$_n$NR"$_9$R"$_{10}$, said C$_{1-7}$alkyl being optionally substituted with one to six of the same or different halogen, NR"$_9$R"$_{10}$, CN, NO$_2$, aryl, said aryl being substituted with one or two groups independently selected from NR"$_9$R"$_{10}$, OH, COOR"$_9$, SO$_3$R"$_9$ or OCOR"$_9$; and R"$_7$ and R"$_8$ are each independently H, OH, or taken together is O;

the method comprising the step of:

reacting a bisindolylmaleimide compound of the general formula [II]:

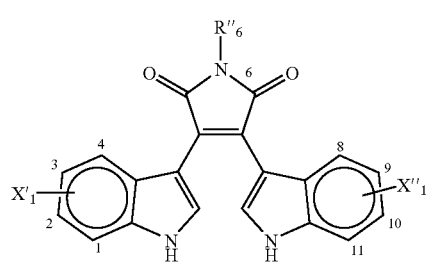

wherein X'$_1$, X"$_1$, R"$_6$, R"$_7$ and R"$_8$ are as described above in formula [I], with an oxidizing agent while sparging with an oxygen containing gas at a temperature and for a time sufficient to yield the indolopyrrolocarbazole compound of the general formula [I].

2. The method according to claim 1, wherein said oxidizing agent is present in an amount of from about 5 mol % to about 100 mol %.

3. The method according to claim 2, wherein said oxidizing agent comprises a copper salt or a palladium salt having an oxidation number of 2+, wherein when said oxidizing agent is said copper salt, then said oxidizing agent is present in an amount of about 100 mol %, and when said oxidizing agent is said palladium salt, then said oxidizing agent is present in an amount of about 5 mol %.

4. The method according to claim 3, wheren said oxidizing agent is selected from the group consisting of CuCl$_2$, Cu(NO$_3$)$_2$, Cu(OAc)$_2$.

5. The method according to claim 4, wherein said oxidizing agent is CuCl$_2$.

6. The method according to claim 2, wherein said oxidizing agent is selected from the group consisting of Pd(OAc)$_2$, PdCl$_2$, Pd(OOCCF$_3$)$_2$, and PdSO$_4$.

7. The method according to claim 5, wherein said oxidizing agent also comprises Pd(OAc)$_2$.

8. The method according to claim 1, further comprising the step of regenerating said oxidizing agent by sequential oxidation reduction reactions converting Pd$^0$ to Pd$^{2+}$ or Cu$^0$ to Cu$^{2+}$.

9. The method according to claim 8, wheren said regeneration step comprises at least one of the following stoichiometric reactions:

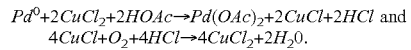

$Pd^0+2CuCl_2+2HOAc \rightarrow Pd(OAc)_2+2CuCl+2HCl$ and
$4CuCl+O_2+4HCl \rightarrow 4CuCl_2+2H_2O$.

10. The method according to claim 1, wherein X'$_1$ is Cl at the 1-position, X'$_{1a}$ is Cl at the 11-position, and R"$_7$ and R"$_8$ together are =O.

11. The method according to claim 1, further comprising the steps of:

(a) reacting a dihalomaleic acid of the general formula [IV]:

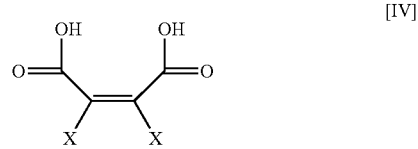

wherein each X is the same or different protecting group selected from a fluorine, a chlorine, a bromine and an iodine atom, with an R"$_6$-substituted amine compound, to form a maleimide compound of the general formula [V]:

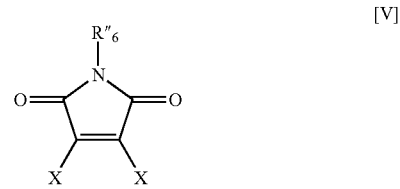

wherein:

R"$_6$, R"$_7$ and R"$_8$ are as defined previously in formula [I]; and (b) reacting said maleimide compound of the general formula [V] with an indolylmetal halide compound of the general formula [VI]:

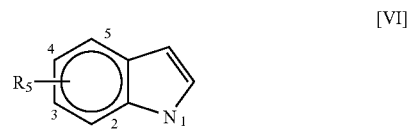

wherein:

$R_5$ is independently selected from H, halogen, OH, —CN, $CF_3$, —$COR''_a$, $NO_2$, $OR''_{11}$, $O(CH_2)_n NR''_9 R''_{10}$, $O(CH_2)_n OR''_9$ and $O(CH_2)_n COOR''_9$, and is present at each of the 2-5 positions;

Y is an alkali metal; and

Z is selected from the group consisting of fluorine, bromine, chlorine, and iodine, to yield the bis-indolylmaleimide compound of the general formula [II].

12. The method according to claim 11, wherein Y is magnesium.

13. A method of synthesizing a rebeccamycin analog of general formula [III] or a pharmaceutically acceptable salt thereof:

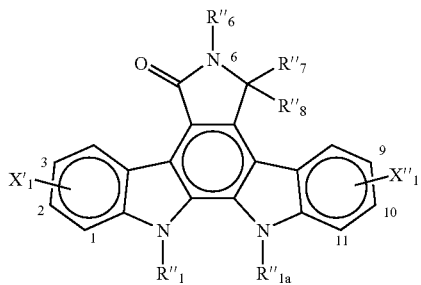

[III]

wherein:

$R''_6$ is H, $C_{1-7}$alkyl, aryl, arylalkyl, $OR''_{10}$, $NR''_9 R''_{10}$, or $OCO(CH_2)_n NR''_9 R''_{10}$, said $C_{1-7}$ alkyl being optionally substituted with one to six of the same or different halogen, $NR''_9 R''_{10}$, CN, $NO_2$, aryl, said aryl being substituted with one or two groups independently selected from $NR''_9 R''_{10}$, OH, $COOR''_9$, $SO_3 R''_9$ or $OCOR''_9$;

n is an integer of from 0 to 4;

$R''_7$ and $R''_8$ are independently OH or H, or taken together is O;

independently selected $X'_1$ and $X''_1$ are present at each of the 1-4 and 8-11 positions, respectively, and are selected from H, halogen, OH, —CN, $CF_3$, —$COR''_a$, $NO_2$, $OR''_{11}$, $O(CH_2)_n NR''_9 R''_{10}$, $O(CH_2)_n OR''_9$ and $O(CH_2)_n COOR''_9$;

$R''_a$ is H, OH, $C_{1-7}$alkoxy or $NR''_9 R''_{10}$;

$R''_9$ and $R''_{10}$ are independently H, $C_{1-7}$alkyl, $C_{1-7}$cycloalkyl, benzyl, aryl, heteroaryl, any of which groups except H can be substituted with one to six of the same or different halogen, OH, $NH_2$, CN, $NO_2$, —C(=NH)$NH_2$, —CH(=NH), $CH(R''_b)(CH_2)_n$ COOH, $CH(R''_b)(CH_2)_n NH_2$, $COOR''_{12}$, or $R''_9$ and $R''_{10}$ together with the nitrogen atom to which they are attached form a cyclic 5-8 membered non-aromatic ring containing either one or two heteroatoms selected from O, N, or S or $R''_9$ and $R''_{10}$ together form =$CHR''_{11} R''_{12}$;

$R''_b$ is H or COOH;

$R''_{11}$ and $R''_{12}$ are independently hydrogen, $C_{1-7}$ alkyl $C_{1-7}$cycloalkyl, heteroaryl, non-aromatic cyclic 5-8 membered ring containing either one or two heteroatoms selected from O or N, $(CH_2)_n NR''_9 R''_{10}$, $(CH_2)_n OR''_9$ or $(CH_2)_n COOR''_9$, said $C_{1-7}$alkyl being optionally substituted with one to six of the same or different halogen, OH, CN, $NO_2$, aryl or heteroaryl, said aryl or heteroaryl substituted with one or two groups independently selected from $NR''_9 R''_{10}$, OH, $COOR''_9$, $SO_3 R''_9$ or $OCOR''_9$;

$R''_1$ and $R''_{1a}$ are each independently $R''_6$, a pentose group (A) or a hexose group (B) of the formulas:

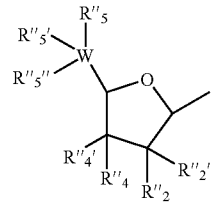

(A)

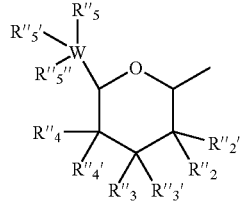

(B)

provided that one of $R''_1$ and $R''_{1a}$ is $R''_6$, and the other is (A) or (B), wherein:

$R''_2$, $R''_3$, $R''_4$, $R''_5$ and $R''_{2'}$, $R''_{3'}$, $R''_{4'}$, $R''_{5''}$ and $R''_{5'}$ are each independently H, $C_{1-7}$alkyl, $C_{1-7}$cycloalkyl, azido, halogen, $NR''_9 R''_{10}$, $NHC(O)NR''_9 R''_{10}$, $NHC(O)OR''$, $OR''$, —$C(O)R''_a$, $SR''$, —$OSO_2 R''_c$, or together form =N—OH, , =O, =$NR''_{12}$, said $C_{1-7}$ alkyl being optionally substituted with one to six of the same or different halogen, CN, $NO_2$, aryl or heteroaryl, said aryl or heteroaryl being substituted with one or two groups independently selected from $NR''_9 R''_{10}$, OH, $COOR''_9$, $SO_3 R''_9$ or $OCOR''_9$;

$R''_c$ is $C_{1-7}$alkoxy or $C_{1-7}$aryl, which may be substituted or unsubstituted; and W is C or N;

the method comprising the steps of:

(a) reacting a bisindolymaleimide compound of the general formula [II]:

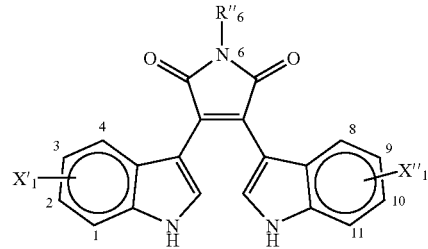

[II]

$X'_1$, $X''_1$, $R''_6$, $R''_7$ and $R''_8$ are as described in formula [III]; with an oxidizing agent while sparging with an oxygen containing gas at a temperature and for a time sufficient to yield the indolopyrrolocarbazole compound of the general formula [I]:

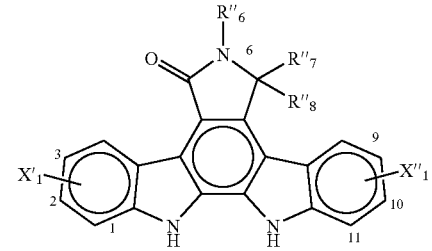

[I]

wherein R"$_6$, R"$_7$, X'$_1$, and X"$_1$, are as described above, and
  (b) glycosylating the indolopyrrolocarbazole compound of the general formula [I] with a sugar moiety selected from a pentose group (A) or a hexose group (B) to yield the rebeccamycin compound of the general fomrula [III], in which one of R"$_1$ or R"$_{1a}$ is a sugar moiety and the other is R"$_6$.

14. The method according to claim 13, wherein said sugar moeity includes at least one protecting group, further including the step of deprotecting said sugar moiety selectively so as to remove said protecting group.

15. The method of claim 13, further comprising the step of reacting the rebeccamycin compound of general formula [I] wherein at least R"$_6$ or one of R"$_1$ and R"$_{1a}$ are H, first with a strong base followed by an R-substituted aminohalide to form a rebeccamycin analog, said R- being selected from the group consisting of: C$_{1-7}$ alkyl, aryl, arylalkyl, OR"$_{10}$, NR"$_9$R"$_{10}$, or OCO(CH$_2$)$_n$NR"$_9$R"$_{10}$, wherein:
  said C$_{1-7}$ alkly is optionally substituted with one to six of the same or different halogen, NR"$_9$R"$_{10}$, CN, NO$_2$, aryl, said aryl being substituted with one or two groups independently selected from NR"$_9$R"$_{10}$, OH, COOR"$_9$, SO$_3$R"$_9$ or OCOR"$_9$.

16. The method according to claim 13, further comprising the step of:
  reacting said rebeccamycin analog of general formula [III], wherein at least one of R"$_6$ and R"$_1$ or R"$_{1a}$ are H, with a strong base followed by a substituted amine halide, said amine halide being substituted with —(CH$_2$)$_n$NR'"$_1$R'"$_2$, wherein n' is an integer of from 1 to 6, and R'"$_1$ and R'"$_2$ are each independently selected from H, unsubstituted and substituted C$_1$-C$_6$ alkyl, aralkyl having 1 to 3 carbons in the alkyl moiety and unsubstituted phenyl or phenyl substituted with 1 to 3 alkyl, alkoxy, hydroxy, halo, carboxyl, alkoxycarbonyl, and amino and mono- and di-lower-alkylamino groups in the aryl moiety, and aryl selected from unsubstituted phenyl and phenyl substituted with 1 to 3 alkyl, alkoxy, hydroxy, halo, amino, mono- and dialkylamino, nitro, carboxyl, alkoxycarbonyl, and cyano groups provided that both R'"$_1$ and R'"$_2$ are not each aryl and, when taken together, R'"$_1$ and R'"$_2$ may be selected from —(CH$_2$—)$_4$— and (CH$_2$)$_2$—R'"$_3$—(CH$_2$)$_2$— to form a 5- or 6 membered ring together with the N-atom wherein R'"$_3$ is selected from CH$_2$, NH, O and S, to yield an R substituted rebeccamycin analog.

17. The method of claim 13 wherein the formula [III] compound is selected from the group consisting of:

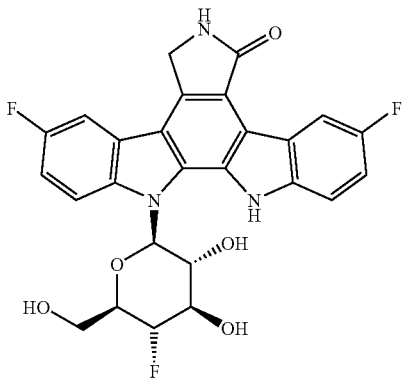

-continued

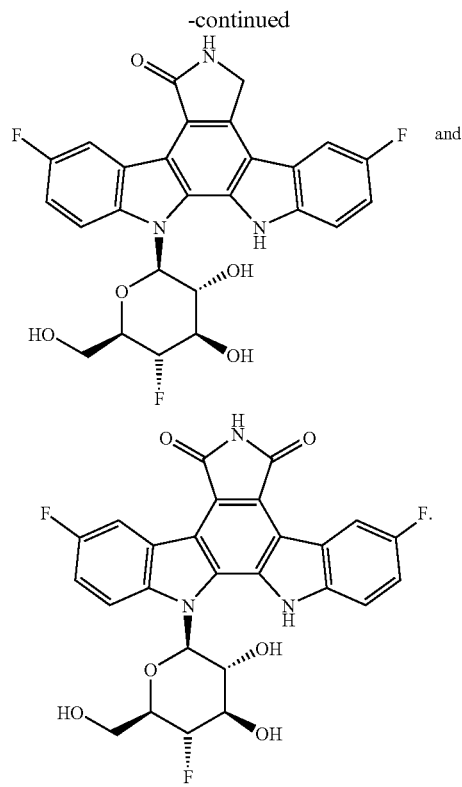

18. The method according to claim 13, wherein said indolopyrrolocarbazole compound is general formula [XI]:

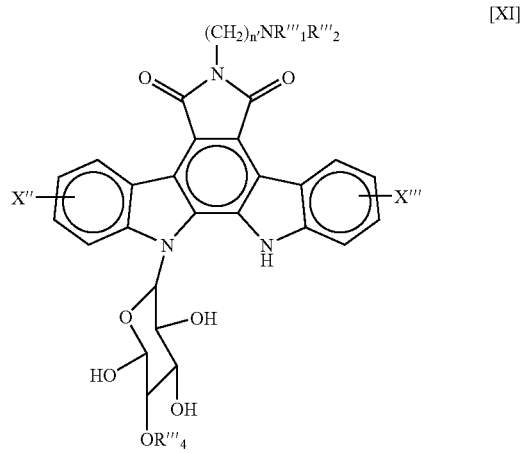

[XI]

and pharmaceutically acceptable acid addition and base salts thereof, wherein:
  n' is an integer from 1 to 6;
  R'"$_1$ and R'"$_2$, independently, are selected from H, unsubstituted and substituted C$_1$-C$_6$ alkyl, aralkyl having 1 to 3carbons in the alkyl moiety and unsubstituted phenyl or phenyl substituted with 1 to 3alkyl, alkoxy, hydroxy, halo, carboxyl, alkoxycarbonyl, and amino and mono- and di-lower-alkylamino groups in the aryl moiety, and aryl selected from unsubstituted phenyl and phenyl substituted with 1 to 3 alkyl, alkoxy, hydroxy, halo, amino, mono- and dialkylamino, nitro, carboxyl, alkoxycarbonyl, and cyano groups provided that both $R'''_1$ and $R'''_2$ are note each aryl and, when taken together, $R'''_1$ and $R'''_2$ may be selected from —$(CH_2)_4$— and $(CH_2)_2$—$R'''_3$—$(CH_2)_2$— to form a 5- or 6 membered ring together with the N-atom wherein $R'''_3$ is selected from $CH_2$, NH, O and S;

$X'''$ is selected from H, F, Cl, Br, $C_1$-$C_3$ alkyl, OH, carboxyl, alkoxycarbonyl and alkoxy wherein the alkyl moiety is $C_1$-$C_3$ alkyl, benzyloxy, amino, and mono- and dialkylamino; and $R'''_4$ is selected from H and $CH_3$.

19. The method according to claim 13 wherein $X'''$ is selected from H, Cl, Br, OH $OCH_3$ and $OCH_2C_6H_5$.

20. The method according to claim 19 wheren n' is selected from the integers 1, 2, and 3; and, $R'''_1$ and $R'''_2$, are independently selected from H, $C_1$-$C_3$alkyl, and —$(CH_2)_4$—.

21. The method according to claim 20 wherein $X'''$ is Cl in each of the 1- and 11-positions.

22. The method according to claim 21 wherein n' is an integer selected from 2 and 3; and $R'''_1$ and $R'''_2$ are each $C_2H_5$.

23. The method according to claim 22 wherein the formula [IV] compound is:

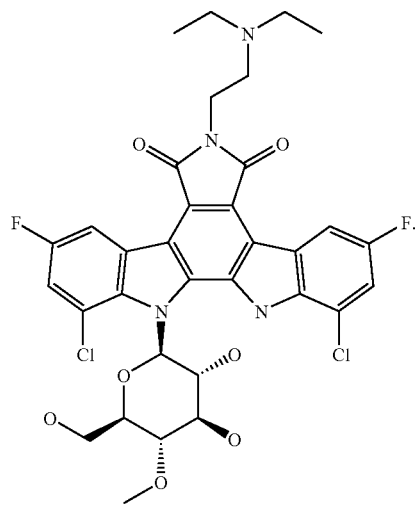

* * * * *